United States Patent [19]
Jitoe et al.

[11] Patent Number: 5,766,212
[45] Date of Patent: Jun. 16, 1998

[54] DISPOSABLE DIAPER

[75] Inventors: Yoshikazu Jitoe, Kagawa-ken; Makoto Suekane, Ehime-ken, both of Japan

[73] Assignee: Uni-Charm Corporation, Ehime-ken, Japan

[21] Appl. No.: 855,666

[22] Filed: May 14, 1997

[30] Foreign Application Priority Data

May 16, 1996 [JP] Japan ................... 8-121355

[51] Int. Cl.$^6$ ................................. A61F 13/15
[52] U.S. Cl. ................................. 604/361
[58] Field of Search ................... 604/359, 360, 604/361

[56] References Cited

U.S. PATENT DOCUMENTS

| | | |
|---|---|---|
| 3,759,261 | 9/1973 | Wang. |
| 4,192,311 | 3/1980 | Felfoldi. |
| 4,705,513 | 11/1987 | Sheldon et al.. |
| 5,690,624 | 11/1997 | Sasaki et al. ............ 604/361 |

FOREIGN PATENT DOCUMENTS

| | | |
|---|---|---|
| 2155356 | 10/1971 | Germany. |
| 3-58416 | 6/1991 | Japan. |
| 94/10958 | 5/1994 | WIPO. |

*Primary Examiner*—Robert A. Clarke
*Assistant Examiner*—John M. Black
*Attorney, Agent, or Firm*—Lowe Hauptman Gopstein & Berner

[57] ABSTRACT

A disposable diaper includes a topsheet, a backsheet and an absorbent core therebetween. The backsheet is made of an air-permeable but liquid-impermeable plastic film having a surface thereof whitened by fine particles of an inorganic substance contained therein. An indicator 18 provided between the backsheet and the absorbent core. The indicator includes a layer of printed ink adapted to be visually revealed when it is wetted with discharged urine and a masking region disposed between the layer of printing ink and the backsheet so as to cover the layer of printed ink, and the masking region contains a surfactant.

6 Claims, 3 Drawing Sheets

FIG.I

DISPOSABLE DIAPER

BACKGROUND OF THE INVENTION

The present invention relates generally to a disposable diapers and particularly to a disposable diaper provided with an indicator allowing discharge of body fluids to be visually recognized from an outside thereof.

Japanese Utility Model Application Laid-Open Publication No. Hei 3-58416 discloses a disposable diaper having a indicator comprising a color change layer formed on an inner surface of a backsheet made of a polyethylene film and a colored liquid-permeable layer formed so as to cover the color change layer. With such indicator of well known art, the color change layer becomes transparent as a quantity of discharged urine attains through the liquid-permeable layer to the color change layer and consequently the color of the liquid-permeable layer can be visually recognized from an outside thereof.

According to the prior art as has been mentioned above, it is tacitly assumed that the backsheet is transparent or translucent. Otherwise, the backsheet would prevent the color of the colored liquid-permeable layer from being visually recognized. However, high transparency of the backsheet causes a situation unacceptable for consumers such that an absorbent core of the diaper smeared with excretions might be seen through the backsheet and, even if the problem is not so extreme, various materials from which the absorbent core and the other components of the diaper are made may be seen through the backsheet. While it will be easy to maintain a selected portion of the backsheet transparent and to make the remaining portion opaque by printing and the like, such measures will unacceptably increase a manufacturing cost of the backsheet.

It is also well known to obtain an air-permeable but liquid-impermeable film by orienting plastic film which contains fine particles of an inorganic substance such as calcium carbonate or barium sulfate and to use this plastic film as the backsheet of the disposable diaper. The resultant film has a surface whitened by said fine particles rising to a surface thereof and presents translucency or transparency desired to conceal the absorbent core smeared with excretions. However, such plastic film can not be effectively used in combination with said known indicator.

SUMMARY OF THE INVENTION

In view of the problems as have been described above, it is a principal object of the invention to provide a disposable diaper so improved that, even when the backsheet comprises an air-permeable but liquid-impermeable oriented plastic film containing fine particles of a suitable inorganic substance, the indicator can be effectively used in combination with such backsheet.

The object set forth above is achieved, according to the invention, by a disposable diaper having a front waist region and a rear waist region, said disposable diaper comprising a liquid-permeable topsheet, a liquid-impermeable backsheet, a liquid-absorbent core disposed between these two sheets, and an indicator provided on one of said front and rear waist regions so as to be visually revealed when the indicator is wetted with body fluids and thereby to make a discharge of body fluids visually recognizable through said backsheet, said disposable diaper being characterized by that:

said backsheet is made of an air-permeable but liquid-impermeable oriented plastic film containing fine particles of an inorganic substance;

said indicator comprises a layer of ink disposed between said backsheet and said absorbent core so as to be visually revealed when said layer of ink is wetted and a covering layer disposed between said backsheet and said layer of ink in tightly contact with said layer of ink so as to cover said layer of ink;

and said covering layer contains a surfactant.

In preferable embodiments of the present invention, said ink covering layer is made of a paper sheet containing said surfactant; said layer of ink is defined by a tissue paper forming a part of said absorbent core and said ink covering layer is defined by the second layer of ink applied onto said tissue paper so as to cover said layer of ink from above; said ink covering layer is bonded to an inner surface of said backsheet; and said backsheet is made of an air-permeable but liquid-impermeable oriented plastic film containing fine particles of titanium oxide, calcium carbonate or barium sulfate.

DESCRIPTION OF THE PREFERRED EMBODIMENTS

Details of a disposable diaper according to the invention will be more fully understood from the following description given hereunder in reference with the accompanying drawings.

Figure 1:
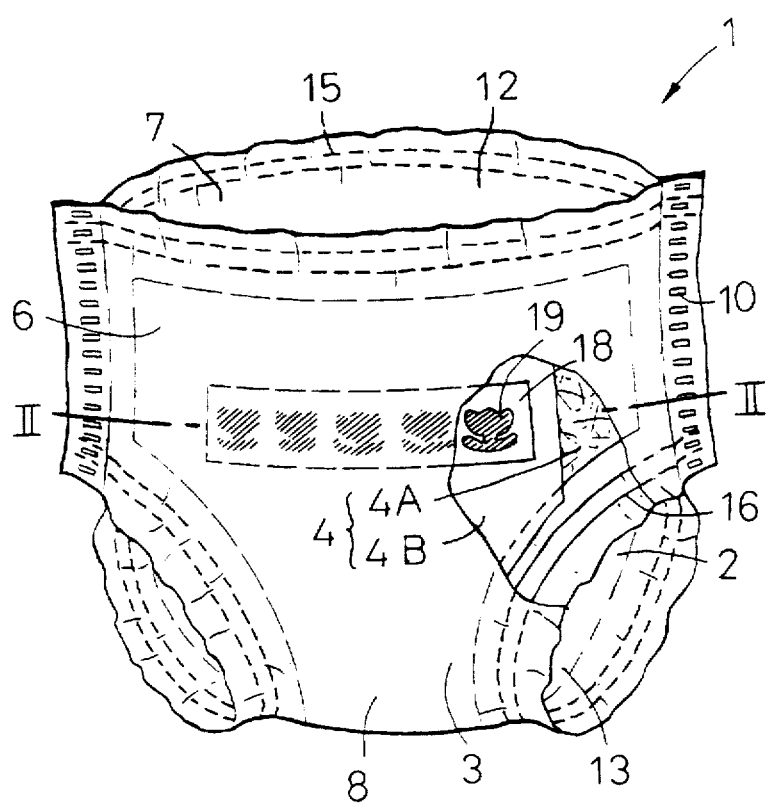
FIG. 1 is a perspective view of a disposable diaper according to the invention as partially broken away.

A pull-on or pants type disposable diaper 1 shown by FIG. 1 in a perspective view as partially broken away comprises a liquid-permeable topsheet 2, a liquid-impermeable backsheet 3 and a liquid-absorbent core 4 disposed between these two sheets 2, 3. The topsheet and backsheet 2, 3 are bonded to each other along portions thereof extending outward beyond a peripheral edge of the absorbent core 4. The diaper 1 has a front waist region 6, a rear waist region 7 and a crotch region 8 extending between these front and rear waist region 6, 7. The front and rear waist region 6, 7 are placed upon each other along transversely opposite side edges thereof with the topsheet 2 inside and bonded to each other by means of joining spots 10 intermittently arranged along the transversely opposite side edges thereof so as to define a waist-opening 12 and a pair of leg-openings 13. The waist- and leg-openings 12, 13 are provided along peripheral edges thereof with waist-surrounding and leg-surrounding elastic members 15, 16, respectively, bonded to an inner surface or inner surfaces of the topsheet 2 and/or backsheet 3 in elastically extended conditions thereof. The topsheet 2 is made of a nonwoven fabric or a perforated plastic film. The backsheet 3 is made of an air-permeable but liquid-impermeable white film having a light transmission of 30–70%, which is obtained by orienting a plastic film containing fine particles of an inorganic substance such as titanium oxide, barium sulfate or calcium carbonate. Such film is well known to those skilled in the art. The absorbent core 4 comprises a mixture 4A of fluff pulp and a hydrocollid material such as superabsorbent polymer particles molded in an hourglass-shape and covered with a tissue paper 4B. The front waist region 6 has an indicator 18 formed between the backsheet 3 and the absorbent core 4, by which occurrence of urine discharge is indicated to the mother of a diaper wearing baby. The indicator 18 is adapted to be visually revealed when the indicator 18 is wetted with urine so that display elements 19 can be visually recognized through the backsheet 3 and thereby the mother can be reliably informed of a timing for diaper exchange.

Figure 2:
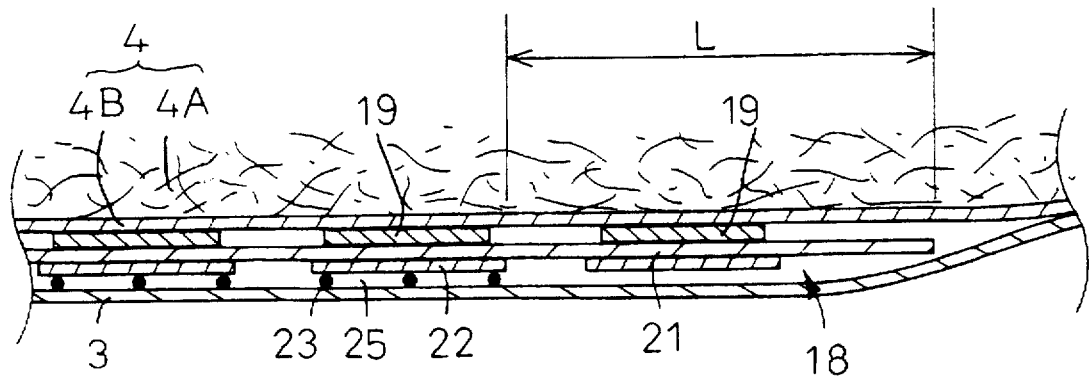
FIG. 2 is a fragmentary sectional view showing an important part of the diaper taken along line II—II in FIG. 1.

FIG. 2 is a fragmentary sectional view taken along a line II—II. The strip-like indicator 18 extending circumferentially of the front waist region 6 as viewed in FIG. 1 comprises a hydrophilic base sheet 21, the previously mentioned display elements 19 printed on an inner surface of the hydrophilic base sheet 21, for example, in a floral pattern, and masking zones 22 printed on an outer surface of the hydrophilic base sheet 21 respectively in sizes at least enough to cover the display elements 19 and cooperating with the white backsheet 3 to conceal the display elements so that the display elements 19 may be practically invisible from the outside as long as the diaper 1 is in a dried condition thereof. The masking regions 22 on the hydrophilic base sheet 21 are bonded to an inner surface of the backsheet 3 by intermittently applied hot melt type adhesives 23 so that the display elements 19 may be maintained by the hydrophilic base sheet 21 in close contact with the backsheet 3. The display elements 19 are preferably maintained in close contact with the absorbent core 4 as shown and, in order to assure such close contact, the display elements 19 themselves or the portions of the hydrophilic base sheet 21 extending adjacent the display elements 19 may be bonded to the tissue paper 4B by means of hot melt adhesive. It should be understood that longitudinally opposite zones of the strip-like indicator 18 each defined by a length L may be left not bonded to the backsheet 3, if it is desired.

The hydrophilic base sheet 21 for the indicator 18 is formed by an uncolored hydrophilic paper, for example, having a basic weight of 15–40 g/m$^2$, a printability for both sides and containing pulp of 50% or higher by weight. Each display element 19 comprises a first coating layer obtained by printing or applying an aqueous ink or a coating material containing 5–20% by weight of a pigment having a color different from those of the hydrophilic base sheet 21, the masking regions 22 and the backsheet 3, 5–35% by weight of light scattering fine particles of an inorganic substance such as silica or alumina, 5–25% by weight of a hydrophilic polyacrylate binder and 30–75% by weight of water onto an inner surface of the hydrophilic base sheet 21. The display element 19 maintains the whiteness due to the light scattering effect by the particles of the inorganic substance as long as the display element 19 is in a dried condition thereof but presents a bright color when the display element 19 is wetted with urine since the light scattering effect decreases and the whiteness is correspondingly lost. Each masking region 22 comprises a second coating layer obtained by printing or applying an aqueous ink or a coating material containing 10–40% by weight of fine particles of an inorganic substance such as silica or alumina, 5–25% by weight of a hydrophilic polyacrylate binder, 0.05–0.5% by weight of a surfactant and 40–85% by weight of water onto an outer surface of the hydrophilic base sheet 21 in a size enough to cover the associated one of display elements 19. The surfactant may be selected from a group consisting of an anionic surfactant such as that known under the trade name of AEROSOL OT, a cationic surfactant, a nonionic surfactant or an amphoteric surfactant. The masking region 22 maintains the whiteness under a light scattering effect thereof and thereby prevents the associated display element 19 from being visually recognized as long as the masking region 22 is in a dried condition thereof. When the masking region 22 is wetted with urine, the light scattering effect decreases until it allows the display element 19 to be visually recognized therethrough and the display element 19 itself presents a bright color. Consequently, the display element 19 can be clearly recognized through the masking region 22 associated with this display element 19. The hydrophilic base sheet 21 has a light scattering characteristic similar to that of the masking regions 22, i.e., effectively conceals the display elements 19 as long as the hydrophilic base sheet 21 is in a dried condition thereof but facilitates the display elements 19 to be clearly recognized therethrough when it is wetted with urine.

The backsheet 3 has, on a surface thereof, fine irregularities formed by fine particles of an inorganic substance rising to the surface and these irregularities present the whiteness under the light scattering effect thereof to conceal the absorbent core 4 as well as the indicator 18 without a demand for any coloring treatment. Consequently, it may sometimes occur that, even when the display elements 19 present a bright color and the hydrophilic base sheet 21 as well as the masking regions 22 facilitate the display elements 19 to be seen through them as these components are wetted with urine, the display elements 19 can not be visually recognized through the backsheet 3. However, the masking regions 22 maintained in close contact with the backsheet 3 contain the surfactant adapted to be dissolved in urine when the masking regions 22 are wetted with urine and to serve as a wetting agent for the inner surface of the backsheet 3 so that the inner surface of the backsheet 3 is also wetted with urine and thereby the light scattering effect decreases enough to facilitate the indicator 18 to be seen through the backsheet 3. It should be understood that content of the surfactant in said second coating layer is preferably 0.05–0.2% by weight per unit area of the backsheet 3. Excessive content of the surfactant, particularly higher than 1% by weight, may cause urine in which the surfactant is dissolved to pass without encountering any serious obstruction through air-permeable fine perforations peculiar to the backsheet 3 and to wet the outer surface thereof. To dispel all these apprehensions, the adhesive 23 is preferably applied intermittently at least onto regions corresponding to the respective display elements 19 and, more preferably, the adhesive 23 is applied over an area less than 70% of each display element 19. Preferably, the adhesive 23 used for this purpose contains no oily ingredient which has a possibility of permeating into the masking regions 22.

The indicator 18 bonded to the backsheet 3 has longitudinally opposite end portions thereof each defined by a length L, which are left not bonded to the backsheet 3, i.e., freely deformable so that these end portions may be apt to come in contact with the absorbent core 4. These freely deformable end portions allow a quantity of discharged urine to permeate from the absorbent core through these end portions into the regions of the display elements 19 bonded to the backsheet 3. The length L of each end portion functioning in this manner is preferably 10 mm or longer.

Figure 3:
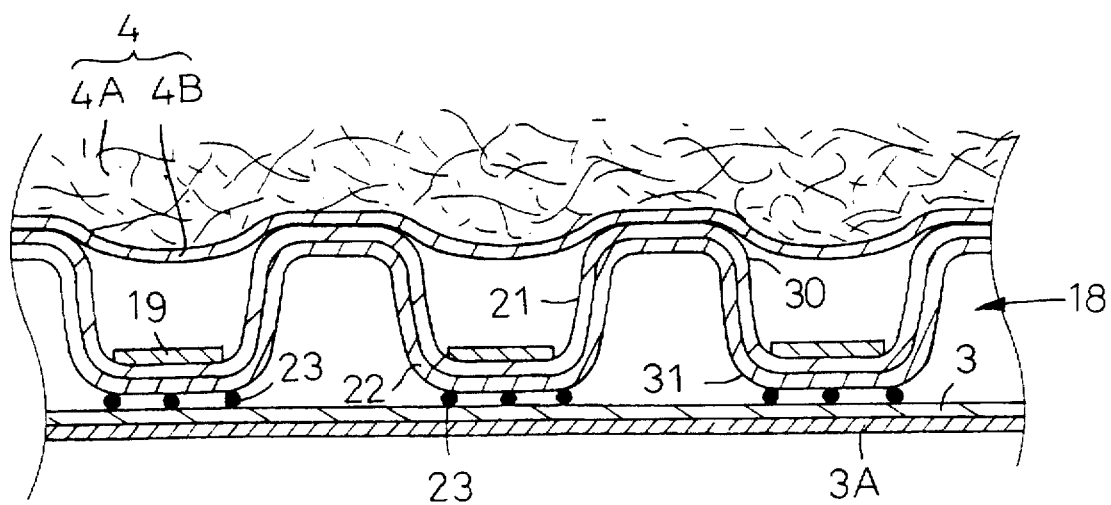
FIG. 3 is a view similar to FIG. 2 showing an arrangement of said important part.

FIG. 3 is a view similar to FIG. 2 showing an alternative arrangement according to the invention. In this arrangement, the indicator 18 describes an undulation repeating rise and fall defined by crests 30 and troughs 31. The indicator 18 comes in contact at the respective crests 30 with the absorbent core 4 and is bonded at the respective troughs 31 to the backsheet 3 by adhesives 23. The display elements 19 are present at the respective troughs 31 and the masking region 22 is formed on the entire outer surface of the hydrophilic base sheet 21. A quantity of discharged urine permeates from the absorbent core 4 through the crests 30 into the display elements 19. An undulant configuration of the indicator 18 allows the indicator 18 to be reliably maintained in contact with the backsheet 3 as well as the absorbent core 4 even when the backsheet 3 is separated from the absorbent core 4. The surfactant contained in the masking area 22 not only helps the backsheet 3 to become rapidly transmissive but also facilitates a quantity of discharged urine to spread from the crests 30 to the troughs 31 and thereby helps the display elements 19 to be rapidly wetted with urine and visually revealed.

Figure 4:
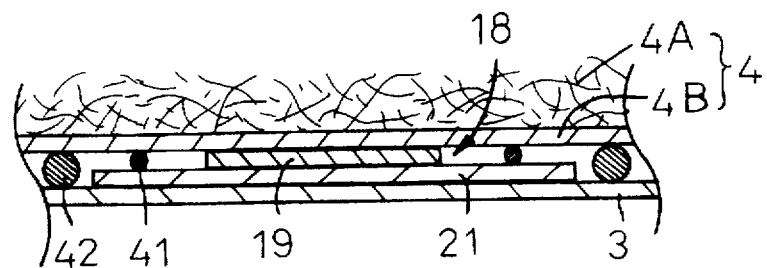
FIG. 4 is a view similar to FIG. 2 showing an alternative arrangement.

FIG. 4 is a view similar to FIG. 2 showing still another arrangement of the invention. In this arrangement, the indicator 18 comprises the hydrophilic base sheet 21 and the display element 19 printed on the inner surface of the hydrophilic base sheet 21. The hydrophyilic base sheet 21 is bonded by hot melt type adhesives 41 to the tissue paper 4B so as to maintain the display element 19 in close contact with the tissue paper 4B and the backsheet 3 is bonded by hot melt adhesives 42 to the tissue paper 4B to maintain the hydrophilic base sheet 21 in close contact with the backsheet 3. The indicator 18 according to this arrangement is suitable for a situation in which the indicator 18 can be concealed only by the hydrophilic base sheet 21, since a basic density of the hydrophilic base sheet 21 is relatively high in this arrangement. The masking regions 22 provided in the arrangements shown by FIGS. 2 and 3 will be unnecessary as far as the hydrophilic base sheet 21 has a sufficient concealing effect as in this arrangement. Even when the hydrophilic base sheet 21 has a concealing effect of the same degree as those provided by the hydrophilic base sheet 21 in the arrangements shown by FIGS. 2 and 3, the hydrophilic base sheet 21 according to the arrangement shown by FIG. 4 is useful also for a situation in which the backsheet 3 has a relatively high content of the inorganic substance particles and/or an orientation or draw ratio and a relatively high concealing effect. In this indicator 18, the same quantity of surfactant as contained in the masking regions 22 according to the arrangements shown by FIGS. 2 and 3 is contained in the hydrophilic base sheet 21.

Figure 5:
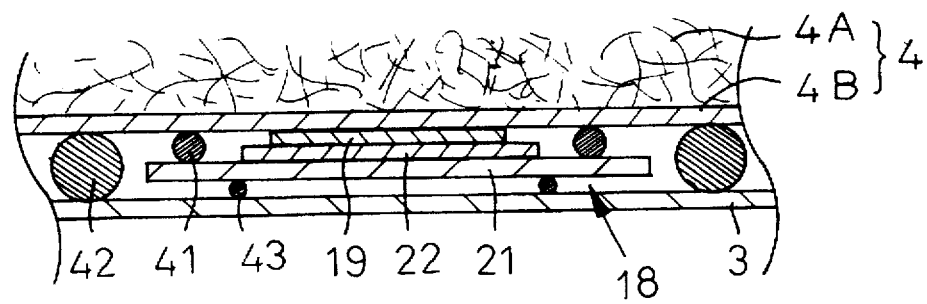
FIG. 5 is a view similar to FIG. 2 showing another alternative arrangement.

FIG. 5 is a view similar to FIG. 2 showing further another arrangement of the invention. In this arrangement, the indicator 18 comprising the hydrophilic base sheet 21, the masking region 22 formed on the inner surface of the hydrophilic base sheet 21, and the display element 19 formed on the inner surface of the masking region 22. The hydrophilic base sheet 21 is bonded by hot melt type adhesives 41 and 43 to the tissue paper 4B and the backsheet 3, respectively, and the backsheet 3 is bonded by hot melt type adhesives 42 to the tissue paper 4B. The hydrophilic base sheet 21 and the masking region 22 contain the surfactant of 0.1–0.2% by weight per unit area of the backsheet 3. It should be understood that any one of hot melt type adhesives 41, 42 and 43 may be eliminated as far as the indicator 18 can be maintained in close contact with the backsheet 3 and the tissue paper 4B. Areas, patterns and locations of these adhesive spots are optional as long as the effect to conceal the display element 19 on the diaper in a dried state thereof is not degraded.

Figure 6:
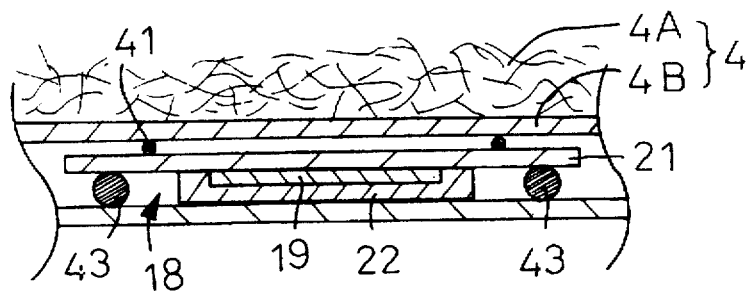
FIG. 6 is a view similar to FIG. 2 showing still another arrangement.

FIG. 6 is a view similar to FIG. 2 showing another variant of arrangement according to the invention. In this arrangement, the indicator 18 comprises the hydrophilic base sheet 21, the display element 19 printed on the outer surface of the hydrophilic base sheet 21 and the masking region 22 formed on said display element 19. The hydrophilic base sheet 21 is bonded by hot melt type adhesives 41 and 43 to the tissue paper 4B and the backsheet 3, respectively. The hydrophilic base sheet 21 comprises a tissue paper containing 100% of pulp, just as the tissue paper 4B of the absorbent core 4 is. The hydrophilic base sheet 21 has a high water absorbability and contains no surfactant. The display element 19 is formed by printing the aqueous ink containing 2.0% by weight of the surfactant onto the outer surface of the hydrophilic base sheet 21 and the masking region 22 is formed by printing the aqueous ink containing 0.05–0.2% by weight of the surfactant onto the outer surface of the hydrophilic base sheet 21 so as to cover the display element 19.

Figure 7:
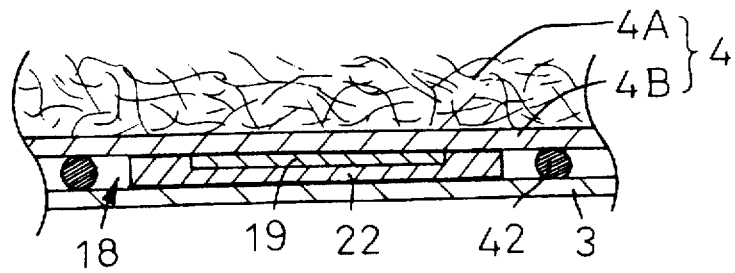
FIG. 7 is a view similar to FIG. 2 showing further another arrangement.

FIG. 7 is a view similar to FIG. 2 showing another variant of the arrangement according to the invention, in which the display element 19 is printed on the tissue paper 4B and the masking region 22 is also printed on the tissue paper 4B so as to cover the display element 19. The tissue paper 4B is bonded by hot melt type adhesives 42 to the backsheet 3.

In the disposable diaper according to the invention, the backsheet is made of an air-permeable but liquid-impermeable plastic film having the surface whitened by the inorganic substance contained therein and rising to the surface. There is provided the indicator on the inner surface of this backsheet. In this indicator, the ink covering layer is disposed between the layer of ink and the backsheet so as to be visually revealed when the ink covering layer is wetted with discharged urine and contains a desired quantity of surfactant. When the indicator is wetted with discharged urine, the surfactant is dissolved in the urine and the whitened inner surface of the backsheet is also wetted therewith until the indicator can be clearly seen through the backsheet. In this manner, the diaper according to the invention allows the air-permeable but liquid-impermeable plastic film to be effectively used in combination with the indicator.

What is claimed is:

1. A disposable diaper having a front waist region and a rear waist region, said disposable diaper comprising a liquid-permeable topsheet, a liquid-impermeable backsheet, a liquid-absorbent core disposed between these two sheets, and an indicator provided on one of front and rear waist regions so as to be visually revealed when the indicator is wetted with discharged body fluids and thereby to make discharge of body fluids visually recognizable through said backsheet, said disposable diaper being characterized by that:

said backsheet is made of an air-permeable but liquid-impermeable oriented plastic film containing fine particles of an inorganic substance;

said indicator comprises a layer of ink disposed between said backsheet and said absorbent core so as to be visually revealed when said layer of ink is wetted with discharged body fluids and an ink covering layer disposed between said backsheet and said layer of ink in tightly contact with said layer of ink so as to cover said layer of ink; and said ink covering layer contains a surfactant.

2. A disposable diaper according to claim 1, wherein said ink covering layer is made of a paper sheet containing said surfactant.

3. A disposable diaper according to claim 1, wherein said covering layer comprises said paper sheet and a second layer of ink applied onto a surface of said paper sheet facing said backsheet and containing said surfactant.

4. A disposable diaper according to claim 1, wherein said layer of ink is defined by a tissue paper forming a part of said absorbent core and said ink covering layer is defined by the second layer of ink applied onto said tissue paper so as to cover said layer of ink from above.

5. A disposable diaper according to claim 1, wherein said ink covering layer is bonded to an inner surface of said backsheet.

6. A disposable diaper according to claim 1, wherein said backsheet is made of an air-permeable but liquid-impermeable oriented plastic film containing fine particles of titanium oxide, calcium carbonate or barium sulfate.

* * * * *